United States Patent
Maas-Brunner et al.

(10) Patent No.: US 6,956,141 B1
(45) Date of Patent: Oct. 18, 2005

(54) METHOD FOR PREPARING ACETYLENE ALCOHOLS AND THEIR SECONDARY PRODUCTS

(75) Inventors: Melanie Maas-Brunner, Mannheim (DE); Jochem Henkelmann, Mannheim (DE); Gerd Kaibel, Lampertheim (DE); Alois Kindler, Grünstadt (DE); Christian Knoll, Neuhofen (DE); Harald Rust, Neustadt (DE); Christian Tragut, Wachenheim (DE); Manfred Stroezel, Ilvesheim (DE); Udo Rheude, Otterstadt (DE); Rudolf Erich Lorenz, Ludwigshafen (DE); Juan Aiscar, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/913,979

(22) PCT Filed: Feb. 22, 2000

(86) PCT No.: PCT/EP00/01425

§ 371 (c)(1),
(2), (4) Date: Jan. 18, 2002

(87) PCT Pub. No.: WO00/50370

PCT Pub. Date: Aug. 31, 2000

(30) Foreign Application Priority Data

Feb. 22, 1999 (DE) ................................. 199 07 532

(51) Int. Cl.$^7$ .................... C07C 33/042; C07C 33/044; C07C 33/046; C07C 33/04
(52) U.S. Cl. ...................... 568/874; 568/861; 568/855; 568/856; 568/873
(58) Field of Search ................................. 568/861, 855, 568/856, 873, 874

(56) References Cited

U.S. PATENT DOCUMENTS

| 2,488,082 A | 11/1949 | Gottfried et al. ............ 260/638 |
| 5,444,170 A | 8/1995 | Vedage ........................ 568/861 |

FOREIGN PATENT DOCUMENTS

| DE | 2 008 675 | 9/1971 |
| DE | 195 00 479 | 7/1995 |
| FR | 950 894 | 10/1949 |
| GB | 1329815 | 9/1973 |

OTHER PUBLICATIONS

Hauxud Shijie (1997) pp. 269-272.

*Primary Examiner*—Elvis O. Price
(74) *Attorney, Agent, or Firm*—Novak Druce & Quigg (57) ABSTRACT

A process for preparing at least one unsaturated alcohol (B) comprises the steps (I) to (III) below:
(I) reaction of at least one alkali metal hydroxide or alkaline earth metal hydroxide with at least one alcohol (A) in at least one organic solvent (L) to give a mixture (G-I) comprising at least the alcohol (A), the solvent (L) and an alkoxide (AL);
(II) reaction of at least one carbonyl compound of the formula R—CO—R' with at least one alkyne of the formula R"—C≡C—H and the mixture (G-I) obtained in step (I) to give a mixture (G-II) comprising at least the alcohol (A), the solvent (L) and an unsaturated alcohol (B);
(III) distillation of the mixture (G-II) obtained in step (II) to give the alcohol or alcohols (B) and a mixture (G-III) comprising the solvent (L) and the alcohol (A),
wherein the solvent (L) obtained in step (III) and the alcohol (A) obtained in step (III) are recycled as a mixture to step (I).

20 Claims, 1 Drawing Sheet

Fig. 1

METHOD FOR PREPARING ACETYLENE ALCOHOLS AND THEIR SECONDARY PRODUCTS

The present invention relates to a multistage process for preparing alcohols from carbonyl compounds and alkynes and also, in a preferred embodiment, to an integrated process for preparing alcohols from carbonyl compounds and alkynes.

Processes for preparing alcohols from carbonyl compounds and alkynes are known in principle. Thus, for example, DE-A 2 008 675 discloses a process for preparing tertiary acetylene glycols by reaction of acetylene with ketones.

U.S. Pat. No. 2,488,082 describes a process for preparing acetylene alcohols in which acetylene is reacted with a ketone in the presence of an alkali metal alkoxide of a primary or secondary saturated alcohol.

FR 950 894 relates to a process for preparing an acetylene alcohol in which acetylene is reacted with a ketone in the presence of an alkali metal alkoxide of a primary or secondary alcohol, where the alcohol has only one oxygen atom in the molecule and is not completely soluble in water under the reaction temperatures chosen.

In Huaxue Shijie 38 (1997) pp. 269–272, Zhou Hongying describes the preparation of methylbutynol by reaction of acetone with acetylene in the presence of potassium isobutoxide as catalyst.

U.S. Pat. No. 620,298 relates to a cyclic process for preparing acetylene alcohols from carbonyl compounds and 1-alkynes, in which a suspension of finely divided KOH in a solvent is used as base. As solvent, this patent discloses an acetal or a polyether which is liquid under normal conditions.

It is an object of the present invention to provide a process for preparing unsaturated and saturated alcohols which is extremely efficient from economic and ecological points of view.

The present invention accordingly provides a process for preparing at least one unsaturated alcohol (B), which comprises the steps (I) to (III) below:

(I) reaction of at least one alkali metal hydroxide or alkaline earth metal hydroxide with at least one alcohol (A) in at least one organic solvent (L) to give a mixture (G-I) comprising at least the alcohol (A), the solvent (L) and an alkoxide (AL);

(II) reaction of at least one carbonyl compound of the formula R—CO—R' with at least one alkyne of the formula R"—C≡C—H and the mixture (G-I) obtained in step (I) to give a mixture (G-II) comprising at least the alcohol (A), the solvent (L) and an unsaturated alcohol (B);

(III) distillation of the mixture (G-II) obtained in step (II) to give the alcohol or alcohols (B) and a mixture (G-III) comprising the solvent (L) and the alcohol (A), wherein the solvent (L) obtained in step (III) and the alcohol (A) obtained in step (III) are recycled as a mixture to step (I).

There are no particular restrictions in respect of the preparation of the mixture (G-I) comprising the solvent (L), the alcohol (A) and the alkoxide (AL) in step (I). It only has to be ensured that (L) and (A) can be added together as starting materials.

In a preferred embodiment, step (I) is carried out in one or more distillation columns in which the alkoxide or alkoxides is/are prepared by azeotropic drying. Here, it is possible, for example, to introduce a mixture of (L) and (A) as a single feed stream. However, it is likewise possible to introduce (L) and (A) separately and to combine the streams only in the column or columns. Of course, it is also possible to use a plurality of suitable solvents (L) and/or a plurality of suitable alcohols (A). In this case, it is conceivable for them to be fed into the column or columns as a single feed stream or in two or more feed streams comprising the respective solvents (L) and/or the respective alcohols (A).

In addition to (L) and (A), an aqueous solution of one or more alkali metal hydroxides and/or alkaline earth metal hydroxides is added as further starting material in one or more feed streams. In this context, the use of alkali metal hydrides and/or alkaline earth metal hydrides and/or of alkali metal alkyl compounds and/or alkaline earth metal alkyl compounds is likewise conceivable.

Should it be necessary in the context of the present invention, the individual feed streams can, of course, be brought to a desired temperature prior to mixing. Such preliminary temperature adjustment is possible in all conceivable process embodiments.

Distillation of water from the reaction mixture of at least one alcohol (A) and at least one alkali metal hydroxide and/or alkaline earth metal hydroxide during step (I) gives a mixture comprising at least one alkali metal alkoxide or alkaline earth metal alkoxide and the organic solvent or solvents (L). This mixture is preferably obtained from the bottom of the column used.

During the further course of step (I), the excess alcohol or alcohols (A) is/are separated off from this mixture by distillation. This separation can be carried out either in the same column in which the alkoxide or alkoxides has/have been prepared or in one or more downstream columns. In a preferred embodiment of the present invention, step (I) is carried out in a single column in which both water and the alcohol or alcohols (A) are distilled off.

According to the present invention, the amount of alcohol (A) separated off is such that the mixture obtained after the removal of water and the incomplete removal of the alcohol or alcohols (A) generally contains from 0 to 55% by weight of alcohol (A). However, the process is preferably carried out so that the alcohol (A) is not quantitatively removed. Rather, the process is carried out so that the mixture obtained after the removal of water and the incomplete removal of the alcohol or alcohols (A) contains from 1 to 55% by weight, preferably from 2 to 10% by weight and particularly preferably about 5% by weight, of alcohol (A).

In the removal of water in step (I), it is conceivable, depending on the chosen solvent (L) and alcohol (A), for a certain proportion of (L) and/or (A) to be distilled off together with the water as a multiphase mixture. If this is the case, it is possible in the process of the present invention for this multiphase mixture comprising water and (L) and/or (A) which has been separated off to be introduced into a phase separator and for the individual phases to be separated. This makes it possible to return (L) and/or (A) which have/has been separated off in this way to step (I) as starting material(s). The aqueous phase which has been separated off in this way can also be used in a further step of the process of the present invention, as described below.

Alcohols (A) which can be used in the process of the present invention are, for example, primary and secondary alcohols having from 4 to 8 carbon atoms, e.g. n-butanol, isobutanol, n-pentanol, 3-methyl-1-butanol, 2-methyl-1-butanol, 2,2-dimethyl-1-propanol, n-hexanol, 2-ethyl-1-hexanol, 2-butanol, 2-pentanol, 3-pentanol, 2-methyl-1-butanol, 2-methyl-2-butanol or cyclohexanol. It is naturally also possible to use compounds of the formula HO—CH$_2$—CH$_2$—OR'", where R'" is chosen so that the respective compound is soluble in the solvent (mixture) used. Particular preference is given to n-butanol and isobutanol, in particular isobutanol.

Organic solvents (L) used are in general aprotic, preferably polar aprotic, solvents. Suitable solvents are, inter alia, aliphatic, cycloaliphatic and/or substituted or unsubstituted aromatic hydrocarbons such as cyclohexane, benzene, toluene, xylene, cumene or p-diisopropylbenzene, acetals of aldehydes and ketones, cyclic or acyclic aliphatic ethers such as symmetric or asymmetric dialkyl ethers of ethane or butane or glycols such as polyalkylene glycols having C$_2$- to C$_6$-alkyl radicals or glycol esters. Dimethyl sulfoxide, N-methylpyrrolidone, dimethylformamide or hexamethylphosphoramide, for example, are likewise suitable. In the process of the present invention, particular preference is given to aromatic hydrocarbons, especially xylene.

Hydroxides preferred for the purposes of the process of the present invention are alkali metal hydroxides, with KOH being particularly preferred. When using an aqueous solution of KOH, preference is given to using a solution which generally contains from 2 to 60% by weight, preferably from 5 to 50% by weight and particularly preferably from 30 to 35% by weight, of KOH.

Subsequent to step (I), the above-described mixture which still comprises a certain proportion of alcohol (A) and of solvent (L) and alkoxide (AL) passed to step (II). In this step (II) of the process of the present invention, at least one carbonyl compound of the formula R—CO—R' is reacted with at least one alkyne of the formula R"—C≡C—H and the mixture (G-I) obtained in step (I) to give an alcohol (B).

In a preferred embodiment of the process of the present invention, the mixture (G-I) comprising the solvent (L), the alcohol (A) and alkoxide (AL) obtained from step (I) is placed in a suitable reactor and the alkyne or alkynes and the carbonyl compound or compounds are introduced.

The introduction of alkyne and/or carbonyl compound can be carried out by all suitable methods. For example, it is possible to combine alkyne and carbonyl compounds before introduction into the reactor to form one feed stream and to introduce this into the reactor. However, it is of course also possible to introduce alkyne and carbonyl compound into the reactor separately from one another as individual feed streams.

Furthermore, if alkyne and carbonyl compound are introduced into the reactor separately as individual feed streams, it is possible for alkyne to be introduced first followed by carbonyl compounds. It is naturally also conceivable for alkyne to be introduced first and then, while continuing to introduce the alkyne, to add the carbonyl compound and introduce alkyne and carbonyl compound in parallel. In a preferred embodiment of the invention, alkyne and carbonyl compound as separate feed streams to step (II) are introduced simultaneously into the mixture (G-I) from step (I). The introduction can in principle be carried out either discontinuously or continuously. It is preferably carried out continuously.

Depending on the chosen temperature at which the reaction in step (II) is to be carried out, it can be useful to bring the individual components to the necessary temperature before they are fed into the reactor, which can conceivably be achieved by all methods known from the prior art. In particular, it may be necessary for the mixture obtained from step (I), which is discharged from the column, to be cooled before it is fed into the reactor for step (II).

To achieve very good mixing of alkyne, carbonyl compound and the alkoxide or alkoxides present in the mixture from step (I), the reaction mixture is stirred in step (II). This stirring can in principle be carried out by all customary methods known from the prior art. However, it is also conceivable for mixing to be carried out completely by means of a specific manner of introduction or for stirring to be supported by such a specific manner of introduction.

In a preferred embodiment of the process of the present invention, the reaction mixture in step (II) is mixed in a mixing apparatus as is described, for example, in DE-C 42 20 239, which is hereby fully incorporated by reference into the present application. All suitable embodiments of the mixing apparatus described there are conceivable. Thus, for example, alkyne, carbonyl compound and the mixture from step (I) can be introduced as separate streams into the mixing apparatus, which accordingly has to have at least 3 inlets. It is likewise possible for (a) alkyne and carbonyl compound or (b) alkyne and mixture from step (I) or (c) carbonyl compound and mixture from step (I) to be mixed prior to introduction into the mixing apparatus, for example using a mixing apparatus of the type described here, and for the resulting mixture to be introduced as one stream together with (a) mixture from step (I) or (b) carbonyl compound or (c) alkyne as further stream into the mixing apparatus. In this case, the mixing apparatus accordingly has to have at least two inlets. In each of the embodiments, it is conceivable for each of the individual streams which are to be introduced into the mixing apparatus to be, before introduction, divided by means of a suitable apparatus upstream of the mixing apparatus into two or more streams which are subsequently introduced into the mixing apparatus.

Furthermore, two or more mixing apparatuses of the type described here can be used for mixing the individual components which are to be reacted in step (II). For example, mixtures can be prepared in each of these two or more mixing apparatuses and subsequently combined.

If the components which are to be reacted in step (II) are merely to be mixed by means of this apparatus, care has to be taken, in the context of the present invention, that the reaction conditions in the mixing apparatus, for example temperature and pressure, are chosen so that no undesirable reactions occur during mixing.

The mixing apparatus is preferably used as a reaction mixing pump. In the mixing apparatus, the individual components which are to be reacted in step (II) are both mixed and reacted with one another, as described below.

For the reaction in step (II) of alkyne with carbonyl compound and the mixture obtained from step (I), it is generally conceivable for the purposes of the present invention for one or more additional suitable solvents to be added to the organic solvent or solvents (L) and the alcohol or alcohols (A) present in the mixture obtained from step (I).

Carbonyl compounds of the formula R—CO—R' are used in the process of the present invention are, for example, aliphatic, araliphatic or heterocyclic ketones having up to 30 carbon atoms. In these, R and R' can be identical or different and either be two separate radicals or be bridged. It is likewise possible for the radicals R and/or R' to have olifinic or acetylenic functions. Examples which may be mentioned are acetone, isobutyl methyl ketone, 6,10-dimethyl-5-undecen-2-one, 6,11,14-trimethyl-2-pentadecanone, 2-methyl-2-hepten-6-one, 2-methylheptan-6-one, 4-(2,6,6-trimethyl-1-cyclohexenyl)-3-buten-2-one, methyl ethyl ketone, cyclohexanone, acetophenone, benzophenone and 4-piperidone with preference being given to acetone, isobutyl methyl ketone, 6,10-dimethyl-5-undecen-2-one, 6,11,14-trimethyl-2-pentadecanone, 2-methyl-2-hepten-6-one, 2-methylheptan-6-one and 4-(2,6,6-trimethyl-1-cyclohexenyl)-3-buten-2-one.

The use of aldehydes which do not have an acidic hydrogen atom is also conceivable in principle. Here, mention may be made of, inter alia, aldehyde RCHO in which R=H or an alkyl radical having up to 30 carbon atoms. Examples which may be mentioned are ethylhexanal or $CH_2O$. As aldehyde, preference is given to using $CH_2O$.

As alkynes of the formula R"—C≡C—H, mention may be made of those in which R" is selected from the group consisting of hydrogen and aliphatic, araliphatic and aromatic radicals having up to 15 carbon atoms. Examples are acetylene, propyne, 1-butyne, 1-pentyne, 1-hexyne, phenylacetylene, benzylacetylene, 3-methyl-1-butyne or compounds such as If acetylene is used as alkyne in the process of the present invention, it is conceivable for both alkyne monools and alkyne diols to be prepared by reaction with appropriate amounts of carbonyl compound and alkoxide. When an alkyne in which R"≠H is used, alkyne monools are produced.

Of course, it is also conceivable for an alkyne monool to be used as alkyne of the formula R"—C≡C—H in the process of the present invention and an alkyne diol to be prepared therefrom by reaction with the carbonyl compound and the alkoxide. An example which may be mentioned here is the reaction of acetone with methylbutynol.

As alkyne of the formula R"—C≡C—H to be used in the process of the present invention, preference is given to acetylene. In this case, reaction with the carbonyl compounds mentioned above as preferred gives the following alkynols, where the term "alkynol" in principle encompasses all compounds which contain both at least one C—C triple bond and one or more hydroxyl groups:
2,5-dimethylhex-3-yne-2,5-diol (DMHDY), 3-methyl-3-hydroxybut-1-yne, 2,4,7,9-tetramethyl-4,7-dihydroxydec-5-yne, 3,7,11-trimethyl-6-dodecan-1-yn-3-ol, 3,7,11,15-tetramethyl-1-hexadecyn-3-ol, 3,7-dimethyloct-1-yn-6-en-3-ol, 3,7-dimethyloct-1-yn-3-ol, 1-penten-4-yn-3-ol, propynol, but-2-yn-1-ol, but-1-yn-3-ol or the compounds In the preparation of the unsaturated alcohol, the stoichiometric ratio of carbonyl compound to alkyne can be selected essentially freely.

If, for example, alkyne diols are prepared from carbonyl compound and acetylene, preference is given to a stoichiometric ratio of carbonyl compound:acetylene in the range from 1.9:1 to 2.1:1, particularly preferably about 2:1. The stoichiometric ratio of alkoxide:carbonyl compound is preferably in the range from 0.9:1 to 2.1:1, particularly preferably in the range from 1:1 to 1.5:1 and in particular about 1.1:1.

If, for example, alkyne monools are prepared from carbonyl compound and acetylene, preference is given to a stoichiometric ratio of carbonyl compound:acetylene in the range from 1:1 to 0.5:1, particularly preferably about 0.6:1. The stoichiometric ratio of alkoxide:carbonyl compound is preferably in the range from 1:1 to 0.2:1 and in particular about 0.3:1.

The reaction temperature in the reaction of appropriate starting materials to produce alkyne diols in the process of the present invention is preferably in the range from 0 to 50° C., more preferably in the range from 0 to 40° C. and particularly preferably in the range from 25 to 35° C.

The reaction temperature in the reaction of appropriate starting materials to produce alkyne monools in the process of the present invention is preferably in the range from 0 to 50° C., more preferably in the range from 0 to 35° C. and particularly preferably in the range from 0 to 20° C.

The pressures in the abovementioned reactions in the preparation of alkyne monools and alkyne diols in the process of the present invention are preferably in the range from 1 to 20 bar, more preferably in the range from 1 to 5 bar and in particular 1 bar.

The yields of unsaturated alcohol (B) obtained in step (II) of the process of the present invention is preferably at least 75%, more preferably at least 80%, particularly preferably at least 85% and very particularly preferably at least 90%.

As described above, the reaction of step (II) is preferably carried out in a reaction mixing pump as described in DE-C 42 20 239, with the embodiment of the reaction mixing pump not being restricted to the mixing apparatus disclosed there. All conceivable embodiments of an apparatus in which the starting materials of step (II) can be both mixed and reacted are likewise conceivable.

This step (II) finally results in a mixture (G-II) which comprises at least one unsaturated alcohol (B) together with (A) and (L).

In a more preferred embodiment of the present invention, step (II) from which at least one unsaturated alcohol (B) is obtained is followed by a step (II') in which the unsaturated alcohol or alcohols is/are hydrogenated.

Accordingly, the present invention also provides a process for preparing at least one hydrogenated alcohol (C), which comprises the steps (I) to (III') below:
(I) reaction of at least one alkali metal hydroxide or alkaline earth metal hydroxide with at least one alcohol (A) in at least one organic solvent (L) to give a mixture (G-I) comprising at least the alcohol (A), the solvent (L) and an alkoxide (AL);
(II) reaction of at least one carbonyl compound of the formula R—CO—R' with at least one alkyne of the formula R"—C≡C—H and the mixture (G-I) obtained in step (I) to give a mixture (G-II) comprising at least the alcohol (A), the solvent (L) and an unsaturated alcohol (B);
(II') hydrogenation of at least one unsaturated alcohol (B) in the mixture obtained from step (II) to give a mixture (G-II') comprising at least one hydrogenated alcohol (C), the alcohol (A) and the solvent (L);
(III') distillation of the mixture (G-II') obtained in step (II') to give the alcohol or alcohols (C) and a mixture (G-III') comprising the solvent (L) and the alcohol (A),
wherein the solvent (L) obtained in step (III') and the alcohol (A) obtained in step (III') are recycled as a mixture to step (I).

Since, depending on the reactants chosen, an alkyne monool and/or an alkyne diol are/is formed in step (II), various hydrogenations are conceivable in the present process. If, for example, an alkyne monool or an alkyne diol has been obtained, the alkyne monool or alkyne diol can be hydrogenated in a partial hydrogenation to form the corresponding alkenol. However, it is also possible to prepare the respective alkanol by appropriate choice of the hydrogenation conditions.

The respective hydrogenation can in principle be carried out by all suitable processes known from the prior art. Thus, the respective hydrogenation can be carried out in one reactor or in a plurality of reactors connected in series. Here, each reactor can be operated in all conceivable modes; particular mention may be made of the downflow and upflow modes in a fixed-bed reactor. In a preferred embodiment, the hydrogenation takes place in two tube reactors (fixed bed) connected in series, of which the first is operated backmixed in the downflow mode while the second is operated in a single pass in the downflow or upflow mode.

It is possible for the components which are introduced into the hydrogenation reactor or into the plurality of hydrogenation reactors to be preheated or precooled before introduction. This can be carried out, for example, in one or more heat exchangers.

Furthermore, it is possible to regulate the temperature of the hydrogenation reactor or hydrogenation reactors itself/themselves, which can be achieved by all methods known from the prior art. In this way, for example, a falling hydrogenation activity of the catalyst or catalysts used for the hydrogenation, as described below, can be compensated by increasing the reactor temperature. This increase in the reactor temperature can be achieved, for example, by reducing the cooling of the reactor in the case of an exothermic hydrogenation reaction. It is naturally also conceivable for the reactor temperature to be actively increased by means of external heating.

If an alkynol is hydrogenated to an alkenol in the process of the invention, it is possible to use all suitable catalysts known from the prior art for this purpose. Possible catalysts are, inter alia, Pd or Pd/Pb on $CaCO_3$ (Lindlar catalyst). If appropriate, the catalysts such as Pd may be partially poisoned, e.g. by CO, to achieve good selectivities.

If an alkynol is hydrogenated to an alkanol in the process of the present invention, all suitable catalysts known from the prior art can be used for this purpose. Known catalysts include, for example, Pd, Pt, Ni (including Raney Nickel), Co, Ru or Rh catalysts, which can be used in supported form or as all-active catalysts. As supports, it is possible to use all suitable, customary supports such as $Al_2O_3$, $SiO_2$ or C.

In a preferred embodiment of the process, in which one or more alkynols are hydrogenated to the corresponding alkanols, the catalysts used are supported catalysts or all-active catalysts. As active hydrogenation metal, particular mention may be made of the metals of transition groups I, VII and VIII of the Periodic Table. Preference is given to using Ni, Ru, Pd, Pt and Rh.

In a particularly preferred embodiment of the hydrogenation of alkynols to alkanols in the course of the process of the present invention, the catalyst used is a supported Pd catalyst in which the support material comprises aluminum oxide.

The hydrogenation of the alkynols to the respective alkanols in the process of the present invention takes place at pressures of generally from 1 to 300 bar, preferably from 10 to 200 bar, particularly preferably from 15 to 100 bar and very particularly preferably from 20 to 50 bar.

In general, the temperatures in the hydrogenation of alkynols to the respective alkanols in the process of the present invention are in the range from 30 to 250° C., preferably in the range from 50 to 200° C., and particularly preferably in the range from 80 to 160° C.

If alkynols are hydrogenated to the respective alkenols in the process of the present invention, the temperatures in the hydrogenation are generally in the range from 30 to 200° C., preferably in the range from 30 to 150° C. and particularly preferably in the range from 50 to 130° C.

If two or more reactors connected in series are used for the hydrogenation in the process of the present invention, it is conceivable for different pressures and/or different temperatures to be set for the hydrogenation in the individual reactors. Thus, it is possible, for example, for the temperature of a product stream from a first reactor, which has a temperature higher than that of the feed stream to this first reactor because of the heat of reaction liberated, not to be regulated before it is introduced into a second reactor. However, it is naturally also possible to cool the product stream from the first reactor before it is introduced into the second reactor, for example by means of intermediate cooling provided between these two reactors. Thus, for example, it is possible to match the hydrogenation temperature in the second reactor individually to the activity of the catalyst used there.

Of course, it is also conceivable for a mixture of alkenol and alkanol to be prepared from the alkynol. This is possible, for example, by means of appropriate choice of the hydrogenation conditions. A further possibility is to divide the product stream from step (II), which consists of the mixture obtained in step (II), into two or more streams and to hydrogenate each stream in separate reactors, with the hydrogenation conditions then being able to be different in each reactor. In this way, alkenols and alkanols can be prepared from the alkynol in a simple way.

Depending on the hydrogenation conditions, the following alkenols and/or alkanols can be prepared from the above-described, preferably prepared alkynols:

2,5-dimethylhexane-2,5-diol (DMHD), 3-methyl-3-hydroxybut-1-ene, 2-methyl-2-hydroxybutane, 3,7,11-trimethyl-3-hydroxy-1,6-dodecadiene, 3,7,11,15-tetramethyl-hexadec-1-en-3-ol, 3,7-dimethyl-1,6-octadien-3-ol, 3,7-dimethyloct-1-en-3-ol, 3-methyl-1-(2,6,6-trimethyl-1-cyclohexen-1-yl), 1,4-pentadien-3-ol, 3-methyl-1-(2,6,6-trimethyl-1-cyclohexen-1-yl).

Of course, step (II') is not restricted to a hydrogenation of the triple bond of the alkynol or alkynols obtained from step (II). Depending on the chemical structure of the alkyne or alkynes and/or the carbonyl compound or compounds used in step (II), it is also conceivable for the radicals R and/or R' and/or R" to be chemically modified in step (II') by, for example, reactions being carried out on functional groups present in these radicals. Furthermore, it is also conceivable in the context of the process of the present invention for such reactions to be carried out in addition to the hydrogenations described above.

In a further preferred embodiment of the process of the present invention, step (II) as described above is carried out in individual steps (i) to (vi). Accordingly, the present invention also provides a process, as described above, in which step (II) comprises the substeps (i) to (vi) below:

(i) reaction of at least one carbonyl compound of the formula R—CO—R' with at least one alkyne of the formula R"—C≡C—H and the mixture (G-I) obtained in step (I) to give a mixture (M-i);

(ii) hydrolysis of the mixture (M-i) obtained from substep (i) to give a multiphase mixture (M-ii) comprising at least one organic phase;
(iii) separation of the organic phase or phases from the multiphase mixture (M-ii) obtained in substep (ii);
(iv) extraction of the organic phase or phases separated off in step (iii);
(v) neutralization of the organic phase or phases extracted in step (iv) to give a mixture (M-v) comprising at least one alkali metal salt or alkaline earth metal salt;
(vi) separation of the alkali metal salt(s) or alkaline earth metal salt(s) from the mixture (M-v) obtained in substep (v) to give a mixture (G-II) comprising at least the alcohol (A), the solvent (L) and an unsaturated alcohol (B).

The reaction of the carbonyl compound or compounds with the alkyne or alkynes and the mixture (G-I) obtained in step (I), as described above, results initially in a mixture (M-i) which is passed to the substep (ii). In the substep (ii), the unsaturated alcohol or alcohols (B) is/are set free by hydrolysis.

There are in principle no restrictions as to the way in which the hydrolysis is carried out. Thus, for example, it can be carried out in one or more reactors, with the temperature being able to be regulated in the respective reactor if desired. It is possible, for example, for a reactor to be cooled by means of brine. Likewise, cooling of the hydrolysis water is also conceivable and can likewise be carried out by means of all conceivable methods known from the prior art. In general, the reaction mixture is stirred during the hydrolysis, and this can also be carried out by all customary methods of the prior art. For example, a mixing apparatus as is described above and disclosed, for example, in DE-C 42 20 239 can be employed for stirring and mixing.

The aqueous phase used for this hydrolytic substep (ii) results, in a particularly preferred embodiment of the process of the present invention, from the extraction in substep (iv). Of course, further water can be added to it. Both the water used for the hydrolysis and the reaction mixture to be hydrolyzed can be brought to the desired temperature, for example by means of heat exchangers, before being introduced into the hydrolysis reactor or reactors.

The hydrolysis in substep (ii) produces a mixture (M-ii) consisting of at least two phases, namely at least one organic phase and at least one aqueous phase. In substep (iii), the organic phase or phases is/are separated off from this mixture (M-ii). This phase separation can in principle be carried out by all customary methods. If two or more organic phases are present, it is conceivable for these to be separated off together as a multiphase organic mixture or as two or more separate organic phases. It is likewise conceivable, if two or more aqueous phases are present, for these to be separated off together as a multiphase aqueous mixture or as two or more separate aqueous phases.

In a preferred embodiment of the present invention, the hydrolyzed mixture (M-ii) from substep (ii) is introduced into one or more phase separation vessels which can be designed so that the temperature of the multiphase mixture to be fractionated in the separation vessel can be regulated. Phase separation preferably takes place at temperatures in the range from 10 to 80° C., more preferably in the range from 20 to 60° C. and particularly preferably in the region of 40° C.

In a particularly preferred embodiment of the process of the present invention, the aqueous phase or phases having a content of alkali metal hydroxide and/or alkaline earth metal hydroxide in the range from 2 to 60% by weight, preferably in the range from 30 to 35% by weight, is/are returned as starting material to step (I). For a base concentration which makes it possible to prepare the alkoxide or alkoxides (AL) to be achieved in the alkoxide preparation occurring in step (I), it may be necessary to add a further aqueous solution comprising alkali metal hydroxide and/or alkaline earth metal hydroxide in step (I) in addition to the aqueous phase or phases comprising alkali metal hydroxide and/or alkaline earth metal hydroxide obtained from substep (ii).

The organic phase or phases is/are extracted in a subsequent substep (iv). If a single organic phase or a mixture comprising a plurality of organic phases has been separated off in substep (iii), this phase or this mixture is extracted. If a plurality of organic phases have been separated off, it is conceivable, for example, for each individual organic phase to be extracted separately.

In a preferred embodiment of the present invention, the extraction is carried out using the aqueous phase obtained by distillation from step (I). It is naturally also possible for additional water to be added to this aqueous phase.

The extraction can be carried out by all possible methods known from the prior art, for example using a mixing apparatus as is described above and disclosed in DE-C 42 20 239. Mention may be made, inter alia, of the use of columns such as sieve tray columns, pulsating reciprocating tray columns or packed columns. In a preferred embodiment, the extraction is carried out in countercurrent, with the temperature of the material being extracted generally being in the range from 30 to 50° C., preferably about 40° C., during the extraction.

Accordingly, the present invention also provides a process as described above in which the extraction in substep (iv) is carried out as a countercurrent extraction.

In this extraction step (iv), the alkali metal hydroxide(s) or alkaline earth metal hydroxide(s) is/are removed from the organic phase or phases to such an extent that the alkali metal hydroxide and/or alkaline earth metal hydroxide content of the organic phase or phases is less than 1% by weight, preferably less than 0.1% by weight and particularly preferably less than 0.01% by weight.

The aqueous phase resulting from the extraction is, in a preferred embodiment of the process of the present invention, returned to substep (ii).

The extracted organic phase or phases can be neutralized in the further substep (v). The neutralization is carried out by addition of acid, for example phosphoric acid, formic acid, acetic acid, sulfuric acid or carbon dioxide. The use of solid carbon dioxide is also conceivable. Preference is given to using phosphoric acid in the process of the present invention.

In the subsequent substep (vi), the alkali metal salt(s) or alkaline earth metal salt(s) formed in the neutralization is/are separated off from the mixture (M-v) obtained from substep (v). This separation can generally be carried out by all methods known from the prior art. The removal of the salt(s) can be omitted in the process of the present invention if the product from which the salt is removed is subjected to relatively little thermal stress. This is the case, for example, when the unsaturated alcohol or alcohols (B) is not hydrogenated.

In a preferred embodiment of the process of the present invention, the removal of the inorganic salt or salts from the mixture or mixtures (M-v) obtained in substep (v) is carried out by total vaporization of the organic substances using, for example, a thin film evaporator or a falling film evaporator. The organic salt or salts which remain(s) is/are flushed from the vaporizer by means of one or more suitable substances. As substances suitable for this purpose, mention may be made of, for example, polyalkylene glycols such as polyethylene glycol. In a particularly preferred embodiment, a proportion of at least 0.5%, preferably from 1 to 2% and particularly preferably at least from 1 to 10%, of the substances used for flushing out the inorganic salt or salts is recycled.

If the unsaturated alcohol or alcohols (B) is/are not to be hydrogenated in the process of the present invention or if the hydrogenated alcohol or alcohols (C) is/are not sufficiently thermally stable, so that a loss of desired product occurs at the temperatures occurring in total vaporization, the salt(s) can also be removed by means of ion exchange. The ion exchange can be carried out using all suitable methods known from the prior art.

In a further preferred embodiment, the mixture (M-v) obtained from substep (v) is fed to the vaporizer together with the high-boiling bottoms obtained in the distillation in step (III). In this way, residues of desired product present in the high-boiling bottoms are recycled to the process. A further advantage associated with this recycle loop is that the high-boiling bottoms act as lubricant for the vaporizer.

The distillate resulting from the total vaporization of the organic substances is condensed in the process of the present invention. In a preferred embodiment of the process of the present invention, this condensation is carried out in at least two steps, in a more preferred embodiment in two steps. The temperature at which the first condensation step is carried out is generally in the range from 30 to 80° C., preferably in the range from 35 to 50° C. and more preferably 40° C. The temperature at which the second condensation step is carried out is generally in the range from 0 to 40° C., preferably in the range from 5 to 10° C. and more preferably about 10° C.

The mixture (G-II) which is obtained after the condensation steps and comprises the unsaturated alcohol or alcohols (B), (L) and (A) is then passed to step (II') or (III). Here, in the case of a plurality of condensation steps, it is conceivable for only the condensate from one condensation step to be processed further in step (II') and/or (III). However, it is also possible for a plurality of condensate streams to be processed together in step (II') and/or (III).

In step (III) of the present invention, the mixture (G-II) or (G-II') obtained from the preceding step is distilled to give the alcohol or alcohols (B) or (C) prepared in the preceding step. In this distillation, the organic solvent or solvents (L) and the alcohol or alcohols (A) are also separated off. This distillation can once again be carried out by all customary methods known from the prior art. In a preferred embodiment of the process of the present invention, the distillation is carried out in a packed column having a dividing wall.

The solvent(s) (L) and alcohol(s) (A) obtained after the distillation in step (III) are, according to the process of the present invention, recycled as starting materials to step (I), either separately from one another or as a mixture.

In a further preferred embodiment of the present process, the alcohol or alcohols prepared in step (II) or in steps (II) and (II') and obtained by distillation in step (III) or (III') is finished (i.e. converted into the desired form) in a further step (IV).

Accordingly, the present invention also provides a process as described above which comprises the further step (IV):
(IV) finishing of the alcohol or alcohols B or C prepared in step (II) or in steps (II) and (II') and obtained in step (III) or in step (III').

Finishing can be carried out by all customary and known methods of the prior art and can in principle be decided by the most advantageous method of processing and the form in which the finished material is to be obtained.

Each of the steps (I), (II), (II'), (III), (III') and (IV) and also each of the substeps (i) to (vi) can in principle be carried out continuously or batchwise. In a preferred embodiment of the process of the present invention, these steps and substeps are designed so that each step and each substep can be carried out continuously.

The present invention therefore also provides a process as described above in which each step and each substep is carried out as a continuous process.

The present invention likewise provides a process as described above in which the radicals R and R' of the carbonyl compound of the formula R—CO—R' are identical or different and are straight-chain, branched or cyclic, saturated or unsaturated aliphatic radicals.

In this embodiment, preference is given to using acetone or methyl isobutyl ketone as carbonyl compound in the process of the present invention. The present invention therefore also provides a process as described above in which the carbonyl compound of the formula R—CO—R' is acetone or methyl isobutyl ketone.

The alkyne which is preferably used in the process of the present invention is acetylene. Accordingly, the present invention also provides a process as described above in which acetylene is used as alkyne of the formula R"—C≡C—H.

As described comprehensively above, the present invention provides a process for preparing at least one alcohol in which a large number of products resulting from the individual steps and substeps are returned to the process. This provides a cost-saving and ecologically efficient process which is further improved by the preferred continuous operation of each step and each substep.

The present invention therefore also provides an integrated process for preparing at least one unsaturated alcohol (B), which comprises the continuously operated steps (a) to (h) below:
(a) reaction of at least one alkali metal hydroxide or alkaline earth metal hydroxide with at least one alcohol (A) in at least one organic solvent (L) using the aqueous phase (P-d) obtained in step (d) to give a mixture (G-a) comprising at least the solvent (L), the alcohol (A) and an alkoxide (AL) and to give an aqueous phase (P-a) which is passed to step (e);
(b) reaction of at least one carbonyl compound of the formula R—CO—R' with at least one alkyne of the formula R"—C≡C—H and the mixture (G-a) obtained in step (a) to give a mixture (G-b) comprising at least one unsaturated alcohol (B), where the reaction is preferably carried out in a reaction mixing pump;
(c) hydrolysis of the mixture (G-b) from step (b) using the aqueous phase (P-e) obtained in step (e) to give a multiphase mixture (M-c) comprising at least one organic phase and at least one aqueous phase;
(d) separation of the organic phase or phases from the multiphase mixture (M-c) obtained in step (c) to give at least one aqueous phase (P-d) which is recycled to step (a);
(e) countercurrent extraction of the organic phase or phases separated off in step (d) using the aqueous phase (P-a) obtained in step (a) to give an aqueous phase (P-e) which is recycled to step (c);
(f) neutralization of the organic phase or phases obtained in step (e) to give a mixture (G-f) comprising at least one alkali metal salt or alkaline earth metal salt and also at least the alcohol (A), the solvent (L) and the unsaturated alcohol or alcohols (B);

(g) separation of the alkali metal salt(s) or alkaline earth metal salt(s) from the mixture (G-f) obtained in step (f) to give a mixture (G-g) comprising at least the alcohol (A), the solvent (L) and the unsaturated alcohol or alcohols (B);

(h) distillation of the mixture (G-g) obtained in step (g) to give the unsaturated alcohol or alcohols (B), to give a mixture (M-h) comprising the solvent (L) and the alcohol (A) and to give a mixture (G-h) comprising small amounts of the unsaturated alcohol or alcohols (B), where the solvent (L) and the alcohol (A) are recycled as a mixture to step (a) and the mixture (G-h) comprising small amounts of the unsaturated alcohol or alcohols (B) is recycled to step (g).

In addition, the present invention also provides an integrated process for preparing at least one hydrogenated alcohol (C), which comprises the continuously operated steps (a) to (g) as described above and also the continuously operated steps (g') and (h') which are carried out after step (g):

(g') hydrogenation of the unsaturated alcohol or alcohols (B) in the mixture (G-g) obtained from step (g) to give a mixture (G-g') comprising at least the alcohol (A), the solvent (L) and at least one hydrogenated alcohol (C);

(h') distillation of the mixture (G-g') obtained in step (g') to give the hydrogenated alcohol or alcohols (C), to give a mixture (M-h') comprising the solvent (L) and the alcohol (A) and to give a mixture (G-h') comprising small amounts of the hydrogenated alcohol or alcohols (C), where the solvent (L) and the alcohol (A) are recycled as a mixture to step (a) and the mixture (G-h') comprising small amounts of the hydrogenated alcohol or alcohols (C) is recycled to step (g).

Figure 1:
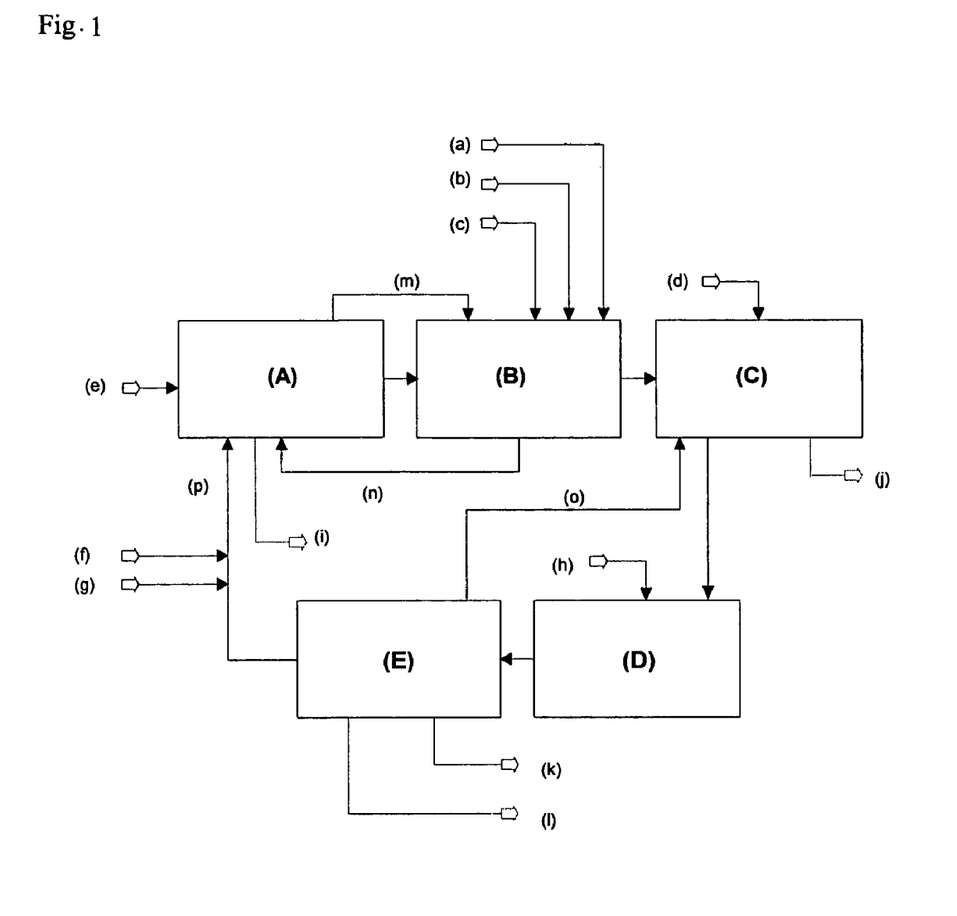

FIG. 1 depicts an embodiment of the process of the present invention for preparing DMHD. The reference letters in the figure have the following meanings:
(A) Preparation of base
(B) Ethynylation/hydrolysis
(C) Salt removal
(D) Hydrogenation
(E) Final distillation
(a) Acetone
(b) Acetylene
(c) Phosphoric acid
(d) Pluriol
(e) KOH
(f) Xylene
(g) i-Butanol
(h) Hydrogen
(i) Low boilers
(j) High boilers
(k) DMHD→finishing
(l) Intermediate boilers
(m) Water
(n) KOH
(o) High boilers
(p) Xylene/i-butanol The following examples illustrate the process of the present invention.

EXAMPLES

Example 1

Preparation of Potassium Isobutoxide

The experiment was carried out in a laboratory column having an internal diameter of 80 mm and provided with 40 bubble cap trays. The working pressure of the column was 900 mbar.

At the top of the column, the vapor obtained was condensed by means of a condenser and conveyed to a phase separator maintained at 50° C. From the phase separator, the organic phase was returned to the column while the aqueous phase was taken off in a level-regulated manner and conveyed to a receiver.

The bottom of the column consisted of a double-walled stirred vessel which was heated by means of heat transfer fluid having a temperature of 218° C. The bottoms were discharged from the column in a level-regulated manner via a bottom outlet valve into a receiver.

220 g/h of an aqueous solution of potassium hydroxide having a concentration of 33% by weight were introduced onto the uppermost tray of the column. The temperature on the fourth tray of the column was measured and regulated to 130° C. by metered addition of a solution of 50% by weight of isobutanol and 50% by weight of a commercial xylene isomer mixture.

The temperature at the top of the column in the experiment was 91° C., and the temperature at the bottom was 140° C. After introduction of a total of 4 857 g of 33% strength by weight KOH and 4 060 g of solvent mixture of 50% by weight of isobutanol and 50% by weight of xylene, 4 727 g of potassium iosbutoxide suspension had been taken off. The KOH conversion was found to be 99.47% and the KOiBu content of the suspension was found to be 5.52 mol/kg. 3 784 g of aqueous phase had been taken off at the phase separator.

Example 2

Preparation of Potassium Isobutoxide

The experiment was carried out in a manner analogous to Example 1.

The temperature at the bottom was 140° C. and the heat transfer jacket of the bottom vessel was operated at 222° C. The pressure at the top of the column was 900 mbar, while the temperature at the top was 91° C. The phase separator at the top was thermostated to 50° C.

220 g/h of aqueous potassium hydroxide having a concentration of 33% by weight of KOH were introduced onto the uppermost tray of the column. A mixture of 45% by weight of isobutanol and 55% by weight of ortho-xylene was introduced onto the uppermost tray of the column. The fourth tray was regulated to 130° C. by regulation of the amount of isobutanol/xylene mixture fed in.

A total of 4 328 g of isobutanol and 3 194 g of 33% strength by weight of KOH were introduced. At the bottom of the column, 4 707 g of potassium isobutoxide suspension were taken off, while 2 663 g of aqueous phase were discharged in the phase separator of the column. The aqueous phase contained 5.37% by weight of isobutanol.

The conversion of KOH was 97.16%, and the isobutoxide content of the suspension was 4.37 mol/kg.

Example 3

Preparation of Potassium Isobutoxide

The experiment was carried out in a manner analogous to Examples 1 and 2.

The temperature at the bottom was 140° C., and the heat transfer bath temperature was 222° C. A temperature at the top of 91° C. was established at a pressure of 900 mbar.

As feed streams, recycled aqueous potassium hydroxide from the hydrolysis of the ethynylation product and solvent mixture from the final distillation were used.

The concentration of the aqueous potassium hydroxide was 32.67% by weight, and the solution contained 0.38% by weight of dimethylhexynediol as main impurity. The composition of the solvent mixture was 39.2% of isobutanol, 48.1% by weight of xylene, 4.5% by weight of water and 2.4% by weight of tert-amyl alcohol.

The aqueous potassium hydroxide was fed in at a rate of 220 g/h, and the flow rate of the solvent mixture introduced was set to 130° C. by regulation of the temperature on the fourth tray of the column.

After addition of 3 585 g of aqueous potassium hydroxide and 4 026 g of the solvent mixture, 4 755 g of potassium isobutoxide suspension and 3 219 g of distillation water had been discharged. The KOH conversion was 98.85%, and the concentration of the base was 4.69 mol/kg of KOiBu. The distillation water contained 2.8% by weight of isobutanol, 2.0% of methylbutanol and 0.9% of acetone as main impurity.

Example 4

Ethynylation (Synthesis of Dimethylhexynediol (DMHDY) by Continuous Ethynylation of Acetone)

The reactor employed was a 1 l Schott double-walled glass reactor provided with a double oblique blade stirrer. The stirrer is operated at 600 rpm. Cooling of the reaction mixture was carried out in an external pumped circuit comprising a gear pump and a double-walled tube cooler. The pump output was in the range from 1 l/min to 4 l/min. The total reaction volume utilized was 1.09 l.

After a running-up phase, 323 g/h of acetone, 73 g/h of acetylene and 1 219 g/h of potassium isobutoxide suspension (5 mol/kg) were pumped continuously into the reactor. All three streams were metered in through an immersed tube onto the lowermost of the two stirring blades. The reaction temperature was maintained in the range from 30° C. to 35° C. by cooling.

An output stream of 1 615 g/h was discharged continuously and introduced via an immersed tube into a 0.25 l Schott double-walled glass reactor provided with a two-stage stirrer. Simultaneously and separately, 670 g/h of water were metered into the reactor. The stirrer of the reactor was operated at 800 rpm. The mixture flowed out over a free overflow into a phase separator. From this, 808 g/h of aqueous phase and 1 555 g/h of organic phase are discharged.

The organic phase comprised 363 g/h of dimethylhexynediol (DMHDY) (yield: 92%) and 10 g/h of acetone (conversion: 97%) and had a residual KOH content of about 90 g/h. The aqueous phase comprised 8 g/h of organic substances and 260 g/h of KOH.

The organic phase was subjected to countercurrent extraction with water in a two-stage mixer-settler unit. The extracted organic phase (1 490 g/h) had a residual KOH content of 0.005 g/h and a water content of 130 g/h. The residual KOH was neutralized by means of phosphoric acid (40% in water).

Example 5

Preparation of Dimethylhexynediol 529 g of a potassium isobutoxide/xylene suspension (4.5 mol/kg), 127 g of acetone and 29 g of acetylene gas were metered continuously and synchronously over a period of one hour into a reaction mixing pump having a nominal capacity of 20 ml. The reaction mixture which was mixed very well in the reaction pump was conveyed via a pump circuit in which a heat exchanger was located. The reaction temperature in the pump was 35° C., that upstream of the heat exchanger was 32° C. and that downstream of the heat exchanger was 28° C. The volume flow in the pumped circuit was in the range from 80 to 100 l/h. From the pump circuit, an after-reaction section led to a hydrolysis vessel where the reaction mixture was hydrolyzed by means of 500 g/h of water. After the organic phase had been separated off and neutralized by means of 22.8 g of phosphoric acid, dimethylhexynediol was obtained at a conversion of 98% and in a yield of 90%. Methylbutynol in a yield of 2.3% was identified as by-product.

Example 6

Preparation of Methylbutynol 529 g of a potassium isobutoxide/xylene suspension (4.5 mol/kg), 127 g of acetone and 58 g of acetylene gas were metered continuously and synchronously over a period of one hour into a reaction mixing pump having a nominal capacity of 20 ml. The reaction mixture which was mixed very well in the reaction pump was conveyed via a pump circuit in which a heat exchanger was located. In this way, the reaction mixture was maintained at a reaction temperature of 20° C. The volume flow in the pumped circuit was in the range from 80 to 100 l/h. From the pump circuit, an after-reaction section led to a hydrolysis vessel where the reaction mixture was hydrolyzed by means of 500 g/h of water. After the organic phase had been separated off and neutralized by means of 22.8 g of phosphoric acid, methylbutynol was obtained at a conversion of 98% and in a yield of 79%. Dimethylhexynediol in a yield of 14% was identified as by-product.

Example 7

Preparation of Methylbutynol Using Catalytic Amounts of Base 52.9 g of a potassium isobutoxide/xylene suspension (0.45 mol/kg), 127 g of acetone (2.18 mol) and 114 g of acetylene gas (4.4 mol) were metered continuously and synchronously over a period of one hour into a reaction mixing pump having a nominal capacity of 20 ml. The reaction mixture which was mixed very well in the reaction pump was conveyed via a pump circuit in which a heat exchanger was located. In this way, the reaction mixture was maintained at a reaction temperature of 10° C. The volume flow in the pumped circuit was in the range from 80 to 100 l/h. From the pump circuit, an after-reaction section led to a hydrolysis vessel where the reaction mixture was hydrolyzed by means of 500 g/h of water. After the organic phase had been separated off and neutralized by means of 2.3 g of phosphoric acid, methylbutynol was obtained at a conversion of 98% and in a yield of 85%. Dimethylhexynediol in a yield of 3% was identified as by-product.

Example 8

Salt Removal by Total Distillation (Salt Removal from the Extracted Crude DMHDY (Dimethylhexynediol) Solution by Total Vaporization)

The total vaporization of the extracted crude DMHDY solution from Example 4 was carried out using a thin film evaporator or falling film evaporator with circulation and two-stage condensation.

The extracted crude DMHDY solution was pumped at a flow rate of 743 g/h (172 g/h of DMHDY) into an evaporator operated at 150 mbar and 170° C. 7 g/h of a high-boiling bottoms fluidizer (PLURIOL®) were mixed into the feed. 722 g/h of vapor (168 g/h of DMHDY) were collected in two condensers maintained at 40° C. and 5° C. In a cold trap operated at −78° C., 4 g/h of organic substance (xylenes, isobutanol) were condensed. Of the readily flowable bottoms (5 g/h), 60–80% were returned to the process.

After condensation of the organic phase in a separation vessel, 12 g/h of water were separated from it. The distillation yield was 97%.

Example 9

Hydrogenation of the Totally Vaporized Crude DMHDY Solution to Give Dimethylhexanediol (DMHD)

The hydrogenation of crude DMHDY solution was carried out continuously over a spherical supported catalyst (diameter: 2–4 mm, 0.25% Pd on $Al_2O_3$) in two tube reactors connected in series. The reactors had a free reactor cross section of 656 $mm^2$, a length of 1.7 m and a fillable volume of 800 ml. The reactors were provided with external heating. The internal temperature of the reactors could be measured at the top, in the middle and in the lower part. Both reactors were charged in the middle with 250 ml of catalyst, and the remaining volume was filled with inert glass spheres.

After running up the reactors, 110 g/h of feed (25.5 g/h of DMHDY) at 80° C. were metered into the first reactor. Hydrogen was likewise introduced from the top downward in a pressure-regulated manner at 30 bar. A constant offgas flow of 2 l/h was established.

After leaving the reactor, part of the output was pumped back to the top of the first reactor. The amount recirculated by pumping was 50 l/h. The other part was pumped to the bottom of the second reactor where it flowed upward. Hydrogen was likewise fed in a pressure-regulated manner at 30 bar through the second reactor from the bottom upward. The offgas flow was 1 l/h. The second reactor had no liquid circulation. After leaving the second reactor, the output (116.2 g/h) was depressurized into a vessel.

The yield of DMHD is 98.5%.

Example 10

Final Distillation

The experiment was carried out in a laboratory column having an internal diameter of 50 mm. The middle section of the column was divided symmetrically into two parts by means of a dividing wall.

The lower, undivided section of the column (height: 30 cm) was packed with mesh packing (surface area: 1 200 $m^2/m^3$). The divided region of the column (height: 90 cm) was packed with wire rings (diameter: 3 mm). A pivoting funnel was installed in the middle section of the column and divided the liquid stream (division ratio of feed side:offtake side=3:7). The uppermost part of the column (height: 60 cm) was provided with laboratory mesh packing (1 200 $m^2/m^3$).

The pressure at the top of the column was 200 mbar. The temperature at the bottom was regulated to 185° C. by means of the amount of bottoms taken off; the temperature of the heating at the bottom was 205° C. The amount taken off at the side offtake was set by regulation of the level of the bottoms. The reflux ratio was set by regulation of the temperature in the middle of the upper column section.

The feed rate was set to 150 g/h. The temperature in the upper part of the column was regulated to 120° C. A total of 3 567 g of a mixture having the composition 60% by weight of isobutanol, 13% by weight of xylene, 13.1% by weight of dimethylhexanediol and 8% by weight of water were fed in. In addition, various trace components, mainly condensation products of acetone, were present in the feed mixture.

At the top, 3 117 g of a low-boiling mixture having a residual dimethylhexanediol content of 0.04% were taken off. At the side offtake, 476 g of dimethylhexanediol having a purity of 99.72% by weight were isolated. The color number of the product was 20 APHA. During the balance period, no high boilers were discharged from the bottom.

Example 11

Final Distillation

The experiment was carried out in a manner analogous to Example 1.

The feed rate was set to 150 g/h. The temperature at the bottom was 202° C.; the temperature at the bottom was regulated at 185° C.

The feed mixture had the following composition: 30% by weight of isobutanol, 23.8% by weight of dimethylhexanediol, 34% by weight of xylene, 2% by weight of methylbutanol, 8% by weight of water. In addition, various trace components, mainly condensation products of acetone, were present in the feed mixture.

At the top, 2 636 g of low boilers having a dimethylhexanediol content of 2.2% were taken off. At the side offtake, 764 g of dimethylhexanediol having a purity of 99.90% and a color number of 9 APHA were isolated. At the bottom, 11 g of high boilers having a DMHD content of 17.1% by weight were taken off during the time of the experiment.

What is claimed is:

1. A process for preparing at least one unsaturated alcohol (B), which comprises the steps (I) to (III) below:
   (I) reaction of at least one alkali metal hydroxide or alkaline earth metal hydroxide with at least one alcohol (A) in at least one organic solvent (L) to give a mixture (G-I) comprising at least the alcohol (A), the solvent (L) and an alkoxide (AL);
   (II) reaction of at least one carbonyl compound of the formula R—CO—R' with at least one alkyne of the formula R"—C≡C—H and the mixture (g-I) obtained in step (I) to give a mixture (G-II) comprising at least the alcohol (A), the solvent (L) and an unsaturated alcohol (B);
   (III) distillation of the mixture (G-II) obtained in step (II) to give the alcohol or alcohols (B) and a mixture (G-III) comprising the solvent (L) and the alcohol (A), wherein the solvent (L) obtained in step (III) and the alcohol (A) obtained in step (III) are recycled as a mixture to step (I), wherein steps (I) to (II) are carried out continuously.

2. A process for preparing at least one hydrogenated alcohol (C), which comprises the steps (I) to (III') below:
   (I) reaction of at least one alkali metal hydroxide or alkaline earth metal hydroxide with at least one alcohol (A) in at least one organic solvent (L) to give a mixture (G-I) comprising at least one alcohol (A), the solvent (L) and an alkoxide (AL);
   (II) reaction of at least one carbonyl compound of the formula R—CO—R' with at least one alkyne of the formula R"—C≡C—H and the mixture (G-I) obtained in step (I) to give a mixture (G-II) comprising at least the alcohol (A), the solvent (L) and an unsaturated alcohol (B);

(II') hydrogenation of at least one unsaturated alcohol (B) in the mixture obtained from step (II) to give a mixture (G-II') comprising at least one hydrogenated alcohol (C), the alcohol (A) and the solvent (L);

(III') distillation of the mixture (G-II') obtained in step (II') to give the alcohol or alcohols (C) and a mixture (G-III') comprising the solvent (L) and the alcohol (A), wherein the solvent (L) obtained in step (III') and the alcohol (A) obtained in step (III') are recycled as a mixture to step (I), wherein steps (I) to (III') are carried out continuously.

3. A process as claimed in claim 1, wherein the step (II) comprises the substeps (i) to (vi) below:
  (i) reaction of at least one carbonyl compound of the formula R—CO—R with at least one alkyne of the formula R"—C≡C—H and the mixture (G-1) obtained in step (I) to give a mixture (M-i);
  (ii) hydrolysis of the mixture (M-i) obtained from substep (i) to give a multiphase mixture (M-ii) comprising at least one organic phase;
  (iii) separation of the organic phase or phases from the multiphase mixture (m-ii) obtained in substep (ii);
  (iv) extraction of the organic phase or phases separated off in step (iii);
  (v) neutralization of the organic phase or phases extracted in step (iv) to give a mixture (M-v) comprising at least one alkali metal salt or alkaline earth metal salt;
  (vi) separation of the alkali metal salt(s) or alkaline earth metal salt(s) from the mixture (M-v) obtained in substep (v) to give a mixture (G-II) comprising at least the alcohol (A), the solvent (L) and an unsaturated alcohol (B).

4. A process as claimed in claim 2, wherein the steps (II) comprises the substeps (i) to (vi) below:
  (i) reaction of at least one carbonyl compound of the formula R—CO—R' with at least one alkyne of the formula R"—C≡C—H and the mixture (G-I) obtained in step (I) to give a mixture (M-i);
  (ii) hydrolysis of a mixture (M-i) obtained from substep (i) to give a multiphase mixture (M-ii) comprising at least one organic phase;
  (iii) separation of the organic phase or phases from the multiphase mixture (M-ii) obtained in substep (ii);
  (iv) extraction of the organic phase or phases separated off in step (iii);
  (v) neutralization of the organic phase or phases extracted in step (iv) to give a mixture (M-v) comprising at least one alkali metal salt or alkaline earth metal salt;
  (vi) separation of the alkali metal salt(s) or alkaline earth metal salt(s) from the mixture (M-v) obtained in substep (v) to give a mixture (G-II) comprising at least the alcohol (A), the solvent (L) and an unsaturated alcohol (B).

5. A process as claimed in claim 3, wherein the extraction in substep (iv) is carried out as a countercurrent extraction.

6. A process as claimed in claim 4, wherein the extraction in substep (iv) is carried out as a countercurrent extraction.

7. A process as claimed in claim 1 which comprises the further step (IV):
  (IV) finishing the alcohol or alcohol B or C prepared in step (II) or in steps (II) and (II') and obtained in step (III) or in step (III').

8. A process as claimed in claim 2 which comprises the further step (IV):
  (IV) finishing of the alcohol or alcohols B or C prepared in step (II) or in steps (II) and (II') and obtained in step (III) or step (III').

9. A process as claimed in claim 3 which comprises the further step (IV):
  (IV) finishing of alcohol or alcohols B or C prepared in step (II) or in steps (II) and (II') and obtained in step (III) or step (III').

10. A process as claimed in claim 4 which comprises the further step (IV):
  (IV) finishing of alcohol or alcohols B or C prepared in step (II) or in steps (II) and (II') and obtained in step (III) or step (III').

11. A process as claimed in claim 5 which comprises the further step (IV):
  (IV) finishing of alcohol or alcohols B or C prepared in step (II) or in steps (II) and (II') and obtained in step (III) or step (III').

12. A process as claimed in claim 6 which comprises the further step (IV):
  (IV) finishing of alcohol or alcohols B or C prepared in step (II) or in steps (II) and (II') and obtained in step (III) or step (III').

13. A process as claimed in claim 1, wherein the radicals R and R' of the carbonyl compound of the formula R—CO—R' are identical or different and are straight-chain, branched or cyclic, saturated or unsaturated aliphatic radicals.

14. A process as claimed in claim 2, wherein the radicals R and R' of the carbonyl compound of the formula R—CO—R' are identical or different and are straight-chain, branched or cyclic, saturated or unsaturated aliphatic radicals.

15. A process as claimed in claim 4, wherein the radicals R and R' of the carbonyl compound of the formula R—CO—R' are identical or different and are straight-chain, branched or cyclic, saturated or unsaturated aliphatic radicals.

16. A process as claimed in claim 14, wherein the carbonyl compound of the formula R—CO—R' is acetone or methyl isobutyl ketone.

17. An integrated process for preparing at least one unsaturated alcohol (B), which comprises the continuously operated steps (a) to (h) below:
  (a) reaction of at least one alkali metal hydroxide or alkaline earth metal hydroxide with at least one alcohol (A) in at least one organic solvent (L) using the aqueous phase (P-d) obtained in step (d) to give a mixture (G-a) comprising at least the solvent (L), the alcohol (A) and an alkoxide (AL) and to give an aqueous phase (P-a) which is passed to step (e);
  (b) reaction of at least one carbonyl compound of the formula R—CO—R' with at least one alkyne of the formula R"—C≡C—H and the mixture (G-a) obtained in step (a) to give a mixture (G-b) comprising at least one unsaturated alcohol (B), where the reaction os preferably carried out in a reaction mixing pump;
  (c) hydrolysis of the mixture (G-b) from step (b) using the aqueous phase (P-e) obtained in step (e) to give a multiphase mixture (M-c) comprising at least one organic phase and at least one aqueous phase;
  (d) separation of the organic phase or phases from the multiphase mixture (M-c) obtained in step (c) to give at least one aqueous phase (P-d) which is recycled to step (a);

(e) countercurrent extraction of the organic phase or phases separated off in step (d) using the aqueous phase (P-a) obtained in step (a) to give an aqueous phase (P-e) which is recycled to step (c);

(f) neutralization of the organic phase or phases obtained in step (e) to give a mixture (G-f) comprising at least one alkali metal salt or alkaline earth metal salt and also at least the alcohol (A), the solvent (L) and the unsaturated alcohol or alcohols (B);

(g) separation of the alkali metal salt(s) or alkaline earth metal salt(s) from the mixture (G-f) obtained in step (f) to give a mixture (G-g) comprising at least the alcohol (A), the solvent (L) and the unsaturated alcohol or alcohols (B);

(h) distillation of the mixture (G-g) obtained in step (g) to give the unsaturated alcohol or alcohols (B), to g I've a mixture (M-h) comprising the solvent (L) and the alcohol (A) and to give a mixture (G-h) comprising small amounts of the unsaturated alcohol or alcohols (B), where the solvent (L) and the alcohol (A) are recycled as a mixture to step (a) and the mixture (G-h) comprising small amounts of the unsaturated alcohol or alcohols (B) is recycled to step (g).

18. An integrated process for preparing at least one hydrogenated alcohol (C), which comprises the continuously operated steps (a) to (g) as claimed in claim 17 and also the continuously operated steps (g') and (h') which are carried out after step (g):

(g') hydrogenation of the unsaturated alcohol or alcohols (B) in the mixture (G-g) obtained from step (g) to give a mixture (G-g') comprising at least the alcohol (A), the solvent (L) and at least one hydrogenated alcohol (C);

(h') distillation of the mixture (G-g') obtained in step (g') to give the hydrogenated alcohol or alcohols (C), to give a mixture (M-h') comprising the solvent (L) and the alcohol (A) and to give a mixture (G-h') comprising small amounts of the hydrogenated alcohol or alcohols (C), where the solvent (L) and the alcohol (A) are recycled as a mixture to step (a) and the mixture (G-h') comprising small amounts of the hydrogenated alcohol or alcohols (C) is recycled to step (g).

19. The process of claim 2, wherein the space-time-yield is about 360 g/h l or greater.

20. The process of claim 2, wherein the yield of unsaturated alcohol (B) obtained in step (II) is at least 90%.

* * * * *

UNITED STATES PATENT AND TRADEMARK OFFICE
CERTIFICATE OF CORRECTION

PATENT NO. : 6,956,141 B1 Page 1 of 1
APPLICATION NO. : 09/913979
DATED : October 18, 2005
INVENTOR(S) : Maas-Brunner et al.

It is certified that error appears in the above-identified patent and that said Letters Patent is hereby corrected as shown below:

In The Claims

Column 19, line 18: "R-CO-R" should read --R-CO-R'--

Column 19, line 41: "R"-C=C-H" should read --R"-C=C-H--

Column 20, line 58: "os" should read --is--

Column 21, line 16: "to g I've" should read --to give--

Column 22, line 20: "360 g/h l" should read --360 g/h·l--

Signed and Sealed this

Tenth Day of April, 2007

JON W. DUDAS
*Director of the United States Patent and Trademark Office*